United States Patent [19]

Garvin et al.

[11] Patent Number: 4,961,557
[45] Date of Patent: Oct. 9, 1990

[54] I.V. BAG STABILIZER

[76] Inventors: Henry M. Garvin, P.O. Box 756;
Christopher M. Horsley, 525 Recold
Rd., both of Walterboro, S.C. 29488

[21] Appl. No.: 395,709

[22] Filed: Aug. 2, 1989

[51] Int. Cl.$^5$ .............................................. A47H 1/10
[52] U.S. Cl. ..................................... 248/318; 211/74;
211/119; 211/162; 248/215; 248/227; 248/340
[58] Field of Search ............ 248/318, 340, 339, 311.3,
248/103, 175, 215, 227, 303, 304; 211/71, 74,
119, 162; 5/503

[56] References Cited

U.S. PATENT DOCUMENTS

| | | | |
|---|---|---|---|
| 2,917,184 | 12/1959 | Beall, Jr. | 248/311.3 X |
| 3,225,953 | 12/1965 | Wolfe | 248/318 X |
| 3,391,891 | 7/1968 | Garden | 248/339 X |
| 3,865,339 | 2/1975 | Von Alven | 248/318 |
| 3,955,682 | 5/1976 | Baren | 248/311.3 X |
| 4,326,648 | 4/1982 | Kieber | 248/311.3 |

Primary Examiner—Ramon O. Ramirez

[57] ABSTRACT

A device designed to stabilize an intravenous solution bag in the vertical position, reducing swinging and bouncing, as the contents of the solution bag are infused into the patient in the pre or post hospital arrival environment.

2 Claims, 1 Drawing Sheet

I.V. BAG STABILIZER

BRIEF DESCRIPTION

The "GARVIN I.V. BAG STABILIZER" provides pre and post hospital medical personnel with a reliable means of keeping an intraveneous solution bag steady as the contents are infused into the patient. The I.V solution bag is placed inside the stabilizer and hung from a pin located inside. The bag is cradled by stabilizing ribs attached to the apparatus to hold it inside. The stabilizer, using the sring loaded adjustable clamp provided on the back, is clamped to the existing bar in the ambulance or stretcher I.V. rack and is held firmly in place to provide a much improved steady drip rate, even over rough terrain.

DRAWING INTERPRETATION

FIG. 1 of the drawing shows the front of the apparatus. It consists of a rigid back (1) with a series of ribs (2) which cradle the I.V. solution bag. A pin (3) is provided at the top to hang the solution bag inside the stabilizer. Two padded hooks (4) that cradle the underside of the existing solution hanging bar are located on both sides of center and work in conjunction with a third hook in the center (5) which is attached to the clamp located on the rear. This hook goes over the top of the bar to provide a clamping action.

FIG. 2 of the drawing shows the back of the stabilizer with the clamp assembly (6). This clamp is of a lever and fulcrum type, adjustable through the use of a threaded portion on the center clamping rod (7) on the opposite end as the hook (5), and the use of a spring (8), and a nut (9). The clamp (6) being attached to the stabilizer through the use of two tabs (10) pressed out of the back of the apparatus.

FIG. 3 of the drawing is a side view of the stabilizer showing how the center hook (5) and end hooks (4) oppose one another and it's slim and efficient design.

DETAILED DESCRIPTION

Figure 1:
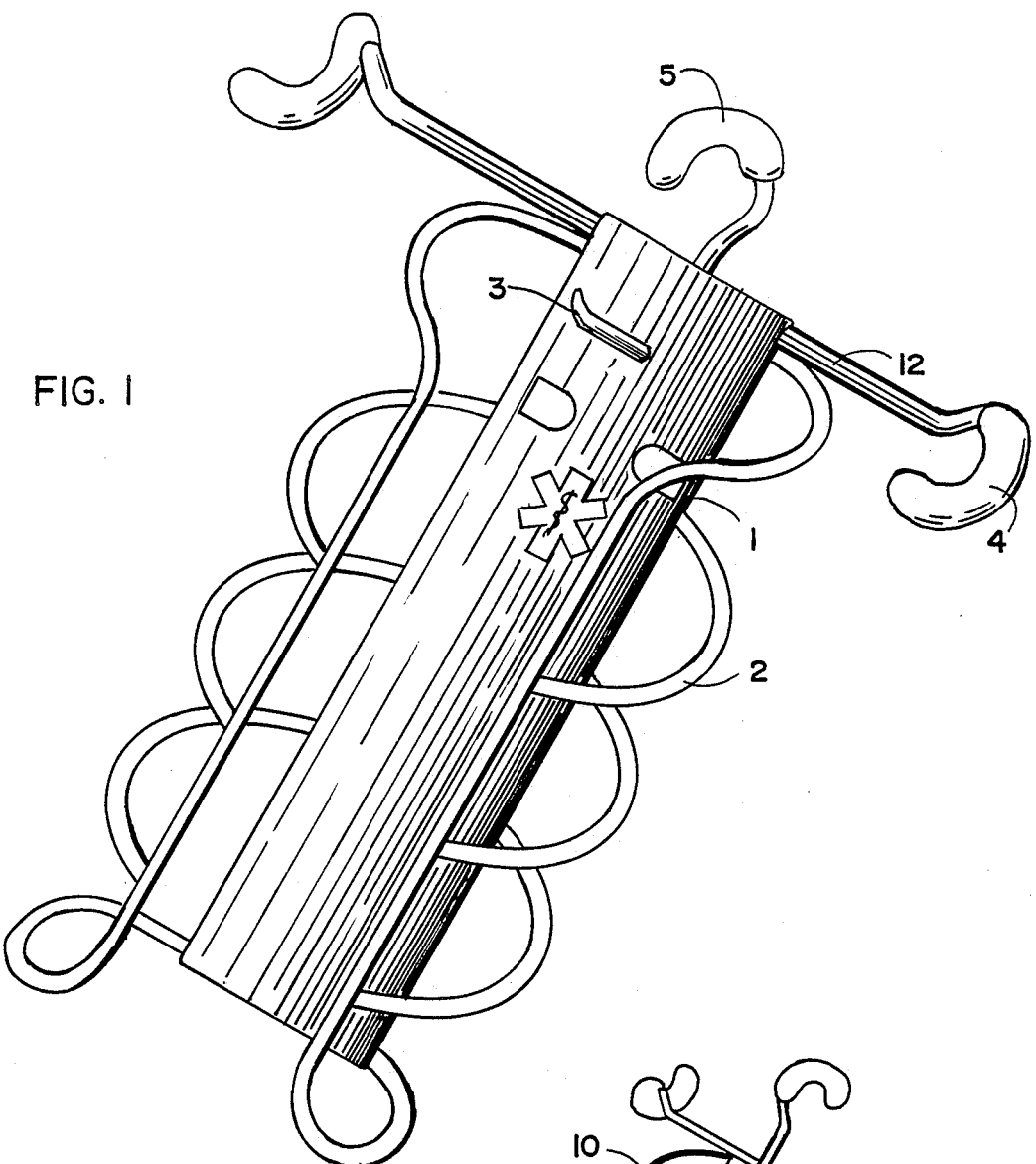
Figure 3:
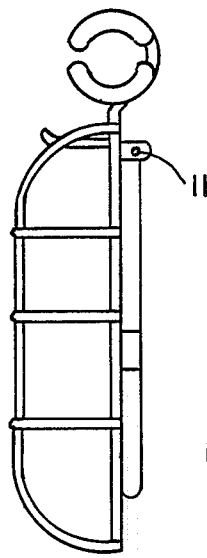
Figure 2:
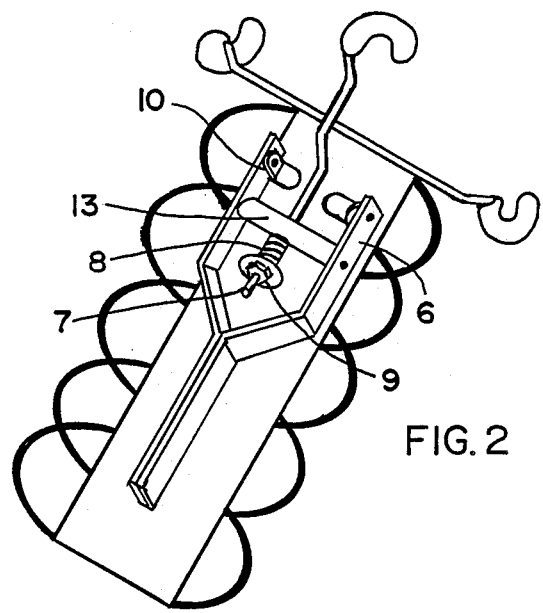

The I.V. BAG STABILIZER can be manufactured from either strong plastic or metal and can be made in different sizes to accommodate different volume I.V. solution bags.

It consists of two major components, the bag cradling portion and the clamping assembly.

The bag cradling portion consists of a rigid back support (1) approximately ⅛" thick with two tabs (10) pressed out toward the back. Each tab shall have a small through hole in it approximately 3/32" diameter to accommodate a pin (11) to attach the clamp (6). The cradling portion shall have a sufficient number of ribs (2) to hold tha bag still while infusion takes place. The bottom of the apparatus is left open to facilitate access to the bag outlets, and a pin (3) located toward the top of the cradling portion extending approximately ¾" with a slight upward curve is provided to hang the bag inside.

The clamping portion consists of a bar (12) attached to the cradling portion which has two padded upswept hooks (4) to attach to the underside of the support bar of the ambulance. The hooks (4) shall be of a 7/16" radius to accommodate a standard bar. These upswept hooks should extend approximately 1" either side of the cradling portion. A lever and fulcrum type clamp (6) is attached to the tabs (10) mentioned earlier with peened pins or rivets (11) which will allow movement. Through a cross member (13) of the lever is a hole which will allow a rod with a downswept padded 7/16" radius hook on one end and a threaded portion on the other (7), to pass through it. There shall be a sufficient number of threads on the one end to allow the hook end of this rod to pass over the bar and close to desired pressure when the clamp assembly is in the clamped position. A rigid spring (8) with an inside diameter slightly larger than the outside diameter of the rod, used in conjunction with a lock nut (9), will provide for pressure adjustment as desired by the end user.

We claim:

1. A device for stabilizing an intravenous solution bag comprising a rigid element having two ends, two sides, a front and a back; a plurality of rib members extending from the sides outwardly and inwardly defining a cradle for the intravenous solution bag; a means for hanging the intravenuos solution bag; and clamnping means for securing the device to a support; wherein the clamping means comprises a bar element secured to one end of the rigid element having padded hooks at the ends of the bar, and a lever and fulcrum type clamp attached to the back of the rigid member via tab means.

2. The device defined in claim 1, wherein the fulcrum type clamp comprises a cross member having an opening, and a rod having two ends, one end passing through the opening and secured by a spring element and a nut, and the other end extending above the bar element ending in a padded hook.

* * * * *